United States Patent [19]

Schach et al.

[11] Patent Number: 5,498,794
[45] Date of Patent: Mar. 12, 1996

[54] PROCESS FOR PREPARING FLUOROANILINES

[75] Inventors: Thomas Schach, Gernsheim; Theodor Papenfuhs, Frankfurt, both of Germany

[73] Assignee: Hoechst Aktiengesellschaft, Frankfurt, Germany

[21] Appl. No.: 386,370

[22] Filed: Feb. 9, 1995

[30] Foreign Application Priority Data

Feb. 11, 1994 [DE] Germany ............... 44 04 342.2
Dec. 16, 1994 [DE] Germany ............... 44 44 903.8

[51] Int. Cl.$^6$ ............................................. C07C 209/22
[52] U.S. Cl. ............................................. 564/417; 564/423
[58] Field of Search ............................. 564/417, 412, 564/423; 546/286, 288, 289, 297, 307, 311; 558/418

[56] References Cited

U.S. PATENT DOCUMENTS

| | | | |
|---|---|---|---|
| 4,140,719 | 2/1979 | Tull et al. ............... | 260/580 |
| 4,294,988 | 10/1981 | Tull et al. ............... | 564/417 |
| 4,298,988 | 10/1981 | Tull ............... | 564/417 |
| 5,041,674 | 8/1991 | Pews ............... | 564/442 |
| 5,144,076 | 9/1992 | Krishnamurti et al. ............... | 564/417 |
| 5,294,742 | 3/1994 | Schach et al. ............... | 564/417 |

FOREIGN PATENT DOCUMENTS

0001825  5/1979  European Pat. Off. .
0506199  9/1992  European Pat. Off. .
0562435  9/1993  European Pat. Off. .

OTHER PUBLICATIONS

European Search Report No. 95101052.9—May 19, 1995.

*Primary Examiner*—Richard L. Raymond
*Attorney, Agent, or Firm*—Connolly and Hutz

[57] ABSTRACT

The invention relates to a process for preparing fluoroanilines of the formula (I)

$$F_nArNH_2 \qquad (I)$$

in which n is 1, 2, 3 or 4, Ar is phenyl, naphthyl or pyridyl, and the remaining substituents on the Ar radical are identical or different and are, independently of each other, hydrogen, halogen, $(C_1-C_1)$-alkyl, phenyl, $NR_2$, OR, CN, CHO, or COR, where R is hydrogen or $(C_1-C_6)$-alkyl, wherein fluoronitrobenzenes of the formula (II)

$$X_mF_nArNO_2 \qquad (II)$$

in which n, Ar and the remaining substituents on the Ar radical have the abovementioned meaning, X is chlorine or bromine and m is 1, 2, 3 or 4, are reacted with hydrogen in the presence of a palladium catalyst, of an amine which is not soluble in water and which also does not form water-soluble hydrohalides, and, where appropriate, of an inert solvent.

32 Claims, No Drawings

PROCESS FOR PREPARING FLUOROANILINES

The present invention relates to an improved process for preparing fluoroanilines by reducing the nitro group of, and catalytically eliminating halogen from, fluoronitrobenzenes which contain bromine and chlorine.

Fluoroanilines are used widely in the sphere of plant protection and as structural elements in the synthesis of pharmaceutical precursors.

Additional substitution of aromatic compounds can only be effected by electrophilic and nucleophilic substitution at quite specific positions which depend on their pattern of substitution which already exists. However, it often happens in the synthesis of aromatic compounds that it is precisely at the less preferred positions that a substituent has to be introduced. A series of strategies for solving this problem do exist. Thus, undesirable positions in the aromatic compound can be blocked with substituents which, on the one hand, are simple to insert into the molecule and, on the other, may equally simply be removed once more. The halogens bromine and chlorine present themselves as substituents of choice; these substituents are very simply introduced into an aromatic system by electrophilic substitution, block this position in the molecule from further attacks, may have an effect on the electronic conditions in the molecule which favors the entry of further substituents, and can be eliminated in a simple manner at the end of the synthesis sequence.

Some fluoronitrobenzenes can be synthesized in an elegant manner from the corresponding chloronitrobenzenes by means of halex reactions. In this case, certain substitution patterns can only be achieved in a roundabout manner, since the corresponding starting compounds can only be synthesized with extreme difficulty. On the other hand, highly substituted chloronitro compounds, which contain the desired chloronitro structural increment in addition to chlorine atoms which are not required, can be prepared in a manner which is simple and technically favorable. Once the reactive chlorine positions have been substituted by fluorine, the remaining chlorine atoms can be removed once more at the end of the synthesis at the same time as the nitro group is reduced. Reductive dehalogenation is available for this purpose.

Apart from these examples, there are many other conceivable situations in which reductive halogen elimination can be employed. For example, isomeric chloronitro compounds can be used in exchange reactions if, after the exchange, the resulting chlorofluoronitro compounds contain the structural increment of the desired fluoroaniline and the subsequent reductive dehalogenation, with reduction of the nitro group, yields the isomerically pure end product.

Nevertheless, when implementing this reaction, a number of processing problems arise which it has hitherto not been found possible to solve in a satisfactory manner. In general, the reactions are carried out in the presence of a catalyst, such as, for example palladium, of a solvent and of an aqueous base, such as, for example, sodium hydroxide solution. Under these reaction conditions, reductive dehalogenations of chloro-/bromofluoronitrobenzenes only provide moderate selectivities and yields (U.S. Pat. No. 4,294,988). As a rule, these reactions only proceed in a manner which is difficult to reproduce (catalyst poisonings) and the selectivity is considerably impaired by the elimination of fluorine. In many cases, it is not possible to avoid corrosion by chloride since reaction temperatures of from 100° to 150° C. are required for most of the dehalogenations and dipolar protic solvents are used.

In the case where elimination of fluoride occurs, two problems come to the fore which are insoluble in many instances. In the first place, it is either not possible in practice, or only possible using a very elaborate separation method, to purify the crude products which are formed and which contain varying contents of fluoride, since their boiling points are practically identical in most cases. Secondly, the fluoride which is formed in the reaction can give rise to further corrosion which can only be countered by making high demands on the reactor material.

In addition, the high nucleophilicity of the base which is used (for example: aqueous NaOH) or of the solvent (water; alcohols in combination with the bases employed) under the reaction conditions leads to the formation of byproducts, resulting in the selectivity of this reaction being further impaired. The occurrence of byproducts can be suppressed to the greatest possible extent by using the customary amines, such as, for example, trimethylamine or triethylamine. The resulting salts of these bases, or the free bases themselves, can either not be recovered at all or only be recovered with difficulty, so that there is substantial organic contamination of the waste water, virtually ruling out industrial implementation of the process.

In view of the multiplicity of side reactions and processing problems associated with the hitherto known preparation processes, there is a great need for an improved synthesis option for preparing highly pure fluoroanilines which, besides providing good to very good yields, also employs precursors which are readily accessible and are available on an industrial scale. While reductive chlorine elimination proves to be a very favorable preparation process, it has hitherto scarcely been possible to implement it industrially due to the high degree of corrosion, the unfavorable product quality and the results of trials which can only be reproduced with difficulty (catalyst poisonings). There was, therefore, a great need to eliminate the described deficiencies and to develop an industrially favorable process.

This object is achieved by a process for preparing fluoroanilines of the formula (I)

$$F_n ArNH_2 \qquad (I)$$

in which n is 1, 2, 3 or 4, Ar is phenyl, naphthyl or pyridyl, and the remaining substituents on the Ar radical are identical or different and are, independently of each other, hydrogen, halogen, $(C_1-C_4)$-alkyl, phenyl, $NR_2$, OR, CN, CHO, or COR, where R is hydrogen or $(C_1-C_6)$-alkyl, wherein fluoronitrobenzenes of the formula (II)

$$X_m F_n ArNO_2 \qquad (II)$$

in which n, Ar and the remaining substituents on the Ar radical have the abovementioned meaning, X is chlorine or bromine and m is 1, 2, 3 or 4, are reacted with hydrogen in the presence of a palladium catalyst, of an amine which is not soluble in water and which also does not form water-soluble hydrohalides, and, where appropriate, of an inert solvent.

The remaining substituents are all the substituents on the Ar radical in the fluoroaniline (I) apart from $F_n$ and $NH_2$, or all the substituents on the Ar radical in the fluoronitrobenzene (II) apart from $X_m$, $F_n$ and $NO_2$. They are, in particular, hydrogen, halogen, $(C_1-C_4)$-alkyl, OR, CN, or COR, preferably hydrogen and halogen.

The starting compounds may be bromine or chlorine compounds, such as, for example: 4-chloro-2,3-difluoronitrobenzene; 5-chloro-2,3-difluoronitrobenzene; 6-chloro-2,3-difluoronitrobenzene; 2-chloro-3,4-difluoronitrobenzene;

2-chloro-4,5-difluoronitrobenzene; 3-chloro-4,5-difluoronitrobenzene; 2-chloro-5-fluoronitrobenzene; 2,6-dichloro-3,5-difluoronitrobenzene; 3,5-dichloro-2,6-difluoronitrobenzene or 3-chloro-2,4-difluoronitrobenzene.

Mixtures of compounds of the formula (II) which, after reaction, yield a homogeneous compound of the formula (I) may also be employed in the process. In this case, these compounds having the same substitution pattern as regards the final compound may also be employed as mixtures of different chlorine and bromine compounds.

3-fluoroaniline, 2,3-difluoroaniline, 3,4-difluoroaniline, 3,5-difluoroaniline and 2,6-difluoroaniline may particularly advantageously be prepared by this process.

It is expedient to use the catalyst on a support material, such as, for example, active charcoal, calcium carbonate, barium sulfate, pumice stone, alumina, kieselguhr, silica gel and/or aluminum oxide. Palladium is preferably used on active charcoal or aluminum oxide as the support material.

It is preferred that the content of palladium in the support catalyst is 0.1–10% by weight, preferably from 0.2–8% by weight, and particularly preferably from 0.5–6% by weight, of palladium, based on the whole catalyst.

The quantity of catalyst required is in the range of 0.1–50 mmol of palladium based on the equivalents of halogen (chlorine/bromine) to be eliminated.

Amines which may be employed are monoamines or polyamines having from two to four amino groups, or mixtures thereof, which have the property that neither the free base nor the base/hydrohalide, which is formed together with the HX which arises, are water-soluble under the conditions of reaction and working-up.

Very satisfactory results are obtained if both the amines which are used and the resulting hydrohalides are liquid.

Amines which are particularly suitable are those of the formula: (III)

$$H_pN(C_rH_{2r+1})_q \qquad (III)$$

where p=0, 1 or 2; q=1,2 or 3, and p+q=3; r=from 5 to 20, preferably from 8 to 15, and the alkyl radicals may be identical or different and branched or unbranched. In particular, p is 0 or 1 and q is 2 or 3.

Highly efficacious aliphatic amines which may be mentioned individually are tri (n-dodecyl) amine; tri (isooctyl) amine; trialkyl (C8/C10) amines, or mixtures thereof.

Although the abovementioned trialkylamines of the said formula (III) are the most suitable, arylamines or aralkylamines may also be employed in principle.

In many cases, it has been found of value to use amine concentrations of from 50 to 500 mol % of amine per equivalent of halogen to be eliminated; the amine is preferably employed in quantities of from 80 to 250 mol %, particularly preferably of from 100 to 150 mol %, per equivalent of halogen to be eliminated.

It is preferable to carry out the reaction in the presence of an inert solvent in which both the starting compounds and the products are readily soluble. The reaction can also be carried out without additional solvent if the starting compounds which are used, and the products, are compounds which are liquid at the reaction temperature and the working-up temperature. Examples of solvents which are used are benzene, toluene, xylene, alkanols ($C_1$–$C_4$): methanol, ethanol,, propanol, polyglycols: ethylene glycol, dialkyl ethers: diethyl ether, methyl ethyl ether, tetrahydrofuran, pentane, hexane, heptane, polyethers: polyethylene glycol dimethyl ether 500, or mixtures of these solvents.

In this process, it is not necessary for a protic solvent (water) to be present.

The process may be carried out either under atmospheric pressure or under excess pressure. It is expedient to carry out the reaction under a hydrogen excess pressure of from 0.1 to 50 bar.

In many cases, it has proved to be of value to carry out the process at temperatures from 0° to 150° C., in particular at from 40° to 120° C. In this context, the use of temperatures which are too low results in a reaction which is slow and incomplete. Temperatures which are set too high can sometimes result in unwanted fluorine elimination or polymer formation.

While it is possible to carry out the reduction of the nitro group and the reductive dehalogenation simultaneously, it is also possible to carry out the process in two steps as a one-pot process. In this case, the halonitro compound is first reduced, in the presence of a catalyst and, where appropriate, of a solvent, to the corresponding haloaniline, and the above-described amine is then added and the reductive dehalogenation is carried out.

The aminehydrohalide which is formed at the end of the reaction may be regenerated in a simple and advantageous manner by treating the crude solution with aqueous base. When this is done, the free amine is formed practically without losses and can be employed once again in the subsequent reaction, without further pretreatment, once the product has been separated off.

By exactly neutralizing the aminehydrohalide, only as much base is consumed as equivalents of fluoroaromatic compound have been formed. The resulting waste water has a neutral reaction.

The used catalyst resulting from the reaction can be reemployed without treatment or can be purified by known purification methods such as, for example, using steam.

The starting compounds for the novel process may be prepared by nitrating the corresponding chlorofluorobenzenes or by means of chlorine/fluorine exchange reactions on chloronitro aromatic compounds. The following examples serve to elucidate the novel process without limiting it thereto.

EXAMPLE (1)

In order to prepare 2,3-difluoroaniline, 96.8 g (0.5 mol) of 3-chloro-2,3-difluoronitrobenzene and 2.0 g of Pd/C (5% strength, 50% water content), as catalyst, are initially introduced, together with 300.0 g of toluene, into a reaction vessel (autoclave). The reaction solution is heated to 60° C. and reduced with hydrogen at this temperature. 295.5 g (0.74 mol) of tri(C8/C10)alkylamine are then added as base, the temperature is raised to 100° C., and reductive dechlorination is carried out. Once the hydrogen uptake has ceased, the mixture is stirred briefly and then cooled to room temperature; the reaction solution is neutralized with sodium hydroxide solution and the catalyst is filtered off with suction from the reaction mixture. After the organic phase has been separated off, it is partially distilled in vacuo and the resulting crude distillate is subsequently fractionated.

The amine mother liquor and also the production residues (first runnings and intermediate cuts) from the fractionation are returned.

Conversion: 100% (according to GC)

Yield: 58.4 g (0.45 mol) of 2,3-difluoroaniline 90.5% based on quantity of 4-chloro-2,3-difluoronitrobenzene employed.

Purity: 98 (GC areas %) 2,3-difluoroaniline

EXAMPLE (2)

In order to prepare 3,5-difluoroaniline, 45.6 g (0.2 mol) of 2,6-dichloro-3,5-difluoronitrobenzene and 2.5 g of Pd/C (5% strength, 50% water content), as catalyst, are initially introduced, together with 100 g of toluene, into a reaction vessel (autoclave). The reaction solution is heated to 50° C. and reduced with hydrogen at this temperature. When the hydrogen uptake begins to slacken, 200 g (0.5 mol) of tri(C8/C10)alkylamine are metered in as base, the temperature is gradually raised to 90° C., and the mixture is maintained at this temperature until no further hydrogen uptake can be observed. The mixture is subsequently stirred briefly and then cooled to room temperature the reaction solution is neutralized with sodium hydroxide solution and the catalyst is filtered off with suction from the reaction mixture. After the organic phase has been separated off, it is partially distilled under reduced pressure and the resulting distillate is dried and then fractionated.

Remaining mother liquor, first runnings and intermediate cuts can be returned in subsequent batches.

Conversion: 99.0% (according to GC)

Yield: 23.7 g (0.18 mol) of 3,5-difluoroaniline 91.8% based on quantity of 2,6-dichloro-3,5difluoronitrobenzene employed.

Purity: 98 (GC areas %) 3,5-difluoroaniline

EXAMPLE (3)

In order to prepare 3,4-difluoroaniline, 96.8 g (0.5 mol) of 2-chloro-3,4-difluoronitrobenzene and 2.5 g of Pd/C (5% strength, 50% water content), as catalyst, are initially introduced, together with 200.0 g of toluene and 4.8 g of tri(C8/C10)alkylamine, into a reaction vessel (autoclave), and the mixture is reduced until hydrogen uptake is complete. 240.0 g (0.60 mol) of tri(C8/C10)alkylamine are then added as base and the temperature is raised gradually from 60° to 100° C., and the mixture is maintained at this temperature until the hydrogen uptake slackens off once more. Once the hydrogen uptake has ceased, the mixture is briefly stirred and then cooled to room temperature; the reaction solution is neutralized with sodium hydroxide solution and the catalyst is filtered off with suction from the reaction mixture. After the organic phase has been separated off, it is partially distilled in vacuo and the resulting crude distillate is subsequently fractionated.

The amine mother liquor and also the production residues (first runnings and intermediate cuts) from the fractionation are returned.

Conversion: 100% (according to GC)

Yield: 55.4 g (0.43 mol) of 3,4-difluoroaniline 85.8% based on quantity of 2-chloro-3,4-difluoronitrobenzene employed.

Purity: 98 (GC areas %) 3,4-difluoroaniline

We claim:

1. A process for preparing a fluoroaniline of the formula (I)

$F_n ArNH_2$       (I)

in which n is 1, 2, 3 or 4, Ar is phenyl, naphthyl or pyridyl, and the remaining substituents on the Ar radical are identical or different and are, independently of each other, hydrogen, halogen, $(C_1-C_4)$-alkyl, phenyl, $NR_2$, OR, CN, CHO, or COR, where R is hydrogen or $(C_1-C_6)$-alkyl, wherein fluoronitrobenzenes of the formula (II)

$X_m F_n ArNO_2$       (II)

in which n, Ar and the remaining substituents on the Ar radical have the abovementioned meaning, X is chlorine or bromine and m is 1, 2, 3 or 4, are reacted with hydrogen in the presence of a palladium catalyst, of an amine which is not soluble in water and which also does not form water-soluble hydrohalides, and, where appropriate, of an inert solvent.

2. The process as claimed in claim 1, wherein 4-chloro-2,3-difluoronitrobenzene; 5-chloro-2,3-difluoronitrobenzene; 6-chloro-2,3-difluoronitrobenzene; 2-chloro-3,4-difluoronitrobenzene; 2 chloro-4,5-difluoronitrobenzene; 3-chloro-4,5-difluoronitrobenzene; 2-chloro-5-fluoronitrobenzene; 2,6-dichloro-3,5-difluoronitrobenzene; 3,5-dichloro2,6-difluoronitrobenzene or 3-chloro-2,4-difluoronitrobenzene are used as suitable fluoronitro aromatic compounds of the formula (II).

3. The process as claimed in claim 1, wherein mixtures of compounds of the formula (II) are employed which, after reaction, yield a compound of the formula (I).

4. The process as claimed in claim 1, wherein 3-fluoroaniline, 3,4-difluoroaniline, 2,3-difluoroaniline, 2,5-difluoroaniline, 3,5-difluoroaniline or 2,6-difluoroaniline are prepared.

5. The process as claimed in claim 1, wherein reaction takes place at temperatures of from 0° to 150° C.

6. The process as claimed in claim 1, wherein palladium on a support material is employed as the palladium catalyst.

7. The process as claimed in claim 6, wherein active charcoal, calcium carbonate, barium sulfate, pumice stone, alumina, kieselguhr, silica gel, aluminum oxide or mixtures thereof are used as support material.

8. The process as claimed in claim 6, wherein the catalyst contains 0.1–10% by weight of palladium, based on the support material used.

9. The process as claimed in claim 1, wherein from 0.01 to 50 mmol of palladium, based on equivalents of halogen to be eliminated, are employed as catalyst.

10. The process as claimed in claim 1, wherein the catalyst is recycled.

11. The process as claimed in claim, 1, wherein alkylamines are employed as amines.

12. The process as claimed in claim 1, wherein an amine of the formula (III)

$H_p N(C_r H_{2r+1})_q$       (III)

where p=0, 1 or 2; q=1, 2 or 3, and p+q=3; r=from 5 to 20 and the alkyl radicals may be identical or different and branched or unbranched, is employed as the amine.

13. The process as claimed in claim 1, wherein tri(n-dodecyl) amine, tri(isooctyl)amine or trialkyl(C8/C10)amines, or mixtures of these amines, are used as amines.

14. The process as claimed in claim 1, wherein the amines which are used are liquid in the reaction medium at the reaction temperature and the working-up temperature.

15. The process as claimed in claim 1, wherein the hydrohalides resulting from the amines which are used are liquid in the reaction medium.

16. The process as claimed in claim 1, wherein the alkylamine is used in quantities of from 50 to 500 mol % based on equivalents of halogen to be eliminated.

17. The process as claimed in claim 1, wherein the amine is recycled.

18. The process as claimed in claim 1, wherein the reaction takes place under standard pressure.

19. The process as claimed in claim 1, wherein benzene, toluene, xylene, C1–C4 alkanols, polyglycols, dialkyl ethers, tetrahydrofuran, pentane, hexane, heptane, polyethers, or mixtures of these solvents, are employed as solvents.

20. The process as claimed in claim 1, wherein the halonitro compound is reduced to the haloaniline in the presence of the catalyst and, where appropriate, of a solvent, and the amine is then added and the reductive dehalogenation is carried out.

21. A process as claimed in claim 1, wherein the reaction takes place at temperatures of from 40° to 120° C.

22. A process as claimed in claim 6, wherein the catalyst contains 0.2 to 8% by weight of palladium, based on the support material.

23. A process as claimed in claim 6, wherein the catalyst contains 0.5 to 6% by weight of palladium, based on the support material.

24. The process as claimed in claim 12, wherein R=8–15.

25. The process as claimed in claim 1, wherein the alkylamine is used in quantities of from 80 to 250 mol % based on equivalents of halogen to be eliminated.

26. The process as claimed in claim 1, wherein the alkylamine is used in quantities of from 100 to 150 mol % based on equivalents of halogen to be eliminated.

27. The process as claimed in claim 1, wherein the reaction takes place under excess pressure.

28. The process as claimed in claim 27, wherein the excess pressure is a hydrogen excess pressure of from 0.1 to 50 bar.

29. A process as claimed in claim 19, wherein the C1–C4 alcohol is methanol, ethanol, or propanol.

30. A process as claimed in claim 19, wherein the polyglycol is ethylene glycol.

31. A process as claimed in claim 19, wherein the dialkyl ether is dimethyl ether or methyl ethyl ether.

32. A process as claimed in claim 19, wherein the polyether is polyethylene glycol dimethyl ether.

* * * * *